(12) United States Patent
Li et al.

(10) Patent No.: US 10,285,447 B2
(45) Date of Patent: May 14, 2019

(54) MOUTHPIECE ASSEMBLY, ATOMIZER AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Yikuan Zhu, Shenzhen (CN); Pengfei Jiang, Shenzhen (CN)

(73) Assignee: SHENZHEN FIRST UNION TECHNOLOGY CO., LTD., Shenzhen, Guangdong Province (CN)

(*) Notice: Subject to any disclaimer, the term of this patent is extended or adjusted under 35 U.S.C. 154(b) by 0 days.

(21) Appl. No.: 15/590,008

(22) Filed: May 8, 2017

(65) Prior Publication Data
US 2017/0238614 A1    Aug. 24, 2017

(30) Foreign Application Priority Data

May 10, 2016    (CN) .................... 2016 2 0414473 U

(51) Int. Cl.
*A24F 13/00* (2006.01)
*A24F 17/00* (2006.01)
*A24F 25/00* (2006.01)
*A24F 11/00* (2006.01)
*A24F 47/00* (2006.01)
*A61M 15/06* (2006.01)
*A61M 15/00* (2006.01)
(Continued)

(52) U.S. Cl.
CPC ......... *A24F 47/008* (2013.01); *A61M 15/002* (2014.02); *A61M 15/0021* (2014.02); *A61M 15/06* (2013.01); *A24D 3/18* (2013.01); *A24F 47/00* (2013.01); *A61M 11/042* (2014.02); *A61M 11/044* (2014.02); *F16L 37/40* (2013.01)

(58) Field of Classification Search
CPC ............................... A24F 47/00; A24F 47/008
USPC .................................................. 131/329, 328
See application file for complete search history.

(56) References Cited

U.S. PATENT DOCUMENTS

2015/0342255 A1* 12/2015 Wu ........................ A61M 15/06
                                                                    131/329
2016/0157522 A1*  6/2016 Zhu ........................ A24F 47/008
                                                                    131/329
(Continued)

*Primary Examiner* — Abdullah A Riyami
*Assistant Examiner* — Thang H Nguyen
(74) *Attorney, Agent, or Firm* — Cheng-Ju Chiang

(57) ABSTRACT

An exemplary mouthpiece assembly includes a mouthpiece. The mouthpiece includes a sucking end, a connecting end, and an air passage. The sucking end defines an air outlet, and the connecting end defines an air inlet. The mouthpiece assembly further includes a partition element dividing the air passage into an air intake chamber and an air outlet chamber. The mouthpiece further includes a sidewall defining at least one first through hole and at least one second through hole, the first through hole is in communication with the air intake chamber, and the second through hole is in communication with the air outlet chamber. The mouthpiece assembly further includes an air adjusting ring defining at least one gap. The air adjusting ring is rotatable relative to mouthpiece, so that an overlapped area among the first through hole, the at least one gap, and the second through hole can be changed.

11 Claims, 8 Drawing Sheets

(51) Int. Cl.
    *A61M 11/04*     (2006.01)
    *A24D 3/18*     (2006.01)
    *F16L 37/40*     (2006.01)

(56) References Cited

U.S. PATENT DOCUMENTS

| | | | |
|---|---|---|---|
| 2017/0105453 A1* | 4/2017 | Li | A24F 47/008 |
| 2017/0224014 A1* | 8/2017 | Fraser | H05B 1/0244 |
| 2017/0347705 A1* | 12/2017 | Li | A24F 47/008 |
| 2017/0367408 A1* | 12/2017 | Pang | A24F 47/008 |
| 2018/0064172 A1* | 3/2018 | Qiu | A24F 47/008 |
| 2018/0077968 A1* | 3/2018 | Qiu | A24F 47/008 |
| 2018/0116295 A1* | 5/2018 | Qiu | A24F 47/008 |

* cited by examiner

MOUTHPIECE ASSEMBLY, ATOMIZER AND ELECTRONIC CIGARETTE HAVING SAME

TECHNICAL FIELD

The present invention relates to electronic cigarettes, and particularly to a mouthpiece, an atomizer and an electronic cigarette using same.

BACKGROUND ART

Nowadays, electronic cigarettes have been in widespread use. However, in a typical electronic cigarette, an amount of aerosol output cannot be adjusted, rendering user unsatisfactory.

What are needed, therefore, are a mouthpiece assembly, an atomizer and an electronic cigarette using same, which can overcome the above shortcomings.

SUMMARY

An exemplary mouthpiece assembly includes a mouthpiece. The mouthpiece includes a sucking end, a connecting end, and an air passage. The sucking end defines an air outlet, and the connecting end defines an air inlet. The mouthpiece assembly further includes a partition element dividing the air passage into an air intake chamber and an air outlet chamber. The mouthpiece further includes a sidewall defining at least one first through hole and at least one second through hole, the first through hole is in communication with the air intake chamber, and the second through hole is in communication with the air outlet chamber. The mouthpiece assembly further includes an air adjusting ring defining at least one gap. The air adjusting ring is rotatable relative to mouthpiece, so that an overlapped area among the first through hole, the at least one gap, and the second through hole can be changed.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
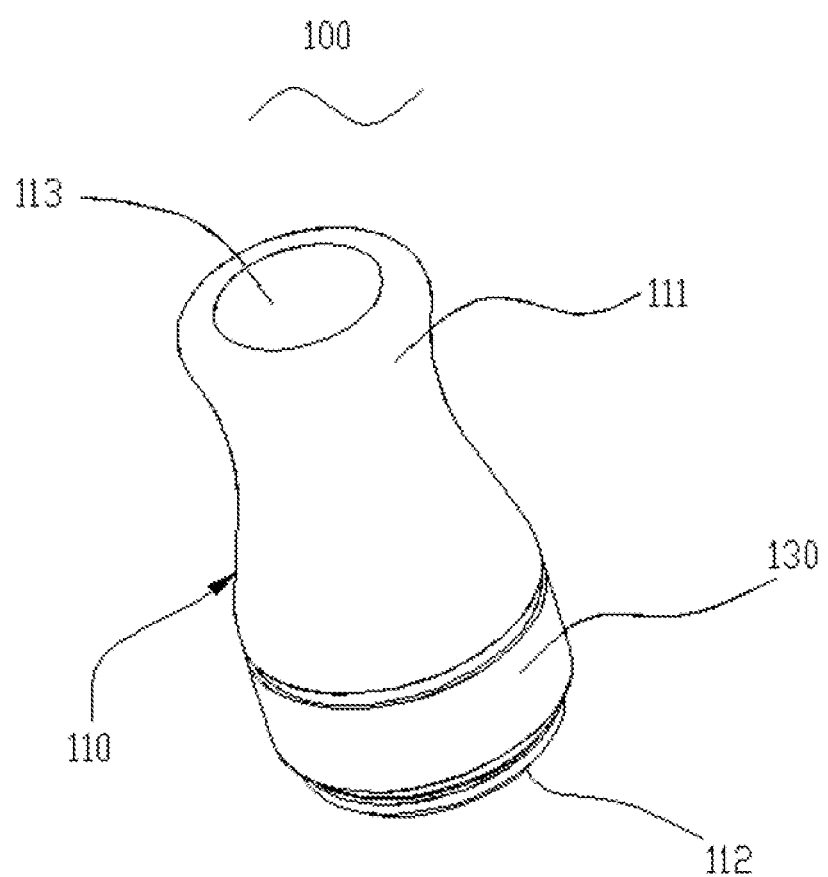
FIG. 1 is a perspective view of a mouthpiece assembly according to a first embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 2:
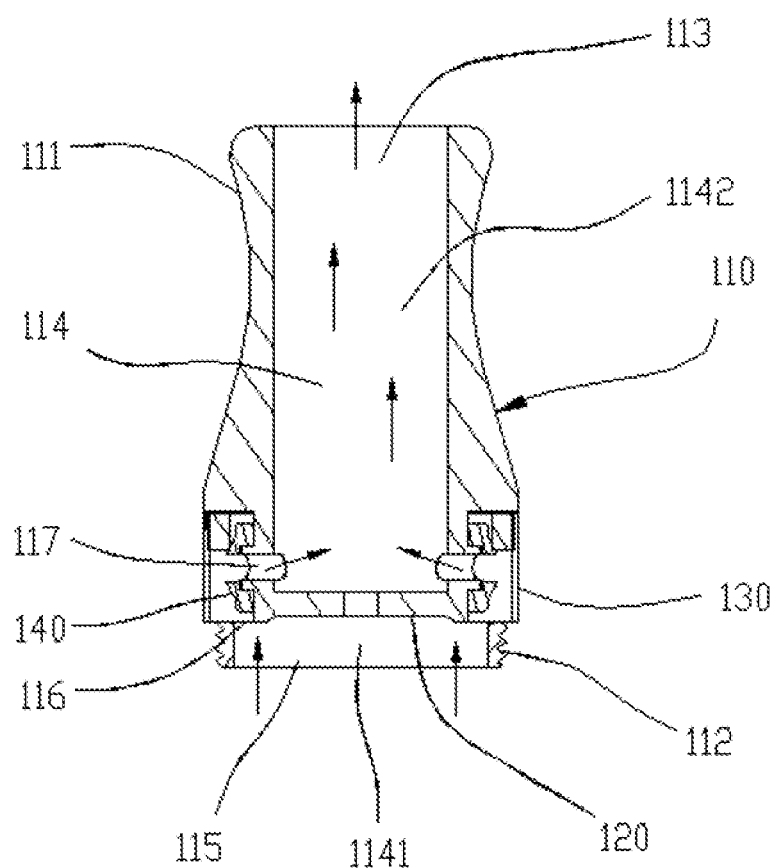
FIG. 2 is a cross-sectional view of the mouthpiece assembly of FIG. 1.

Referring to FIGS. 1-2, a mouthpiece assembly 100 is shown. The mouthpiece assembly 100 includes a mouthpiece 110. The mouthpiece 110 includes a sucking end 111, a connecting end 112 configured (i.e., structured and arranged) for connecting with an external component, and an air passage 114. The sucking end 111 defines an air outlet 113, the connecting end 112 defines an air inlet 115, and both of the air inlet 115 and the air outlet 113 are in communication with the air passage 114. A partition element 120 is further provided in the air passage 114, and divides the air passage 114 into an air intake chamber 1141 and an air outlet chamber 1142. The mouthpiece 110 includes a sidewall defining two first through holes 116, and two second through holes 117. The two first through holes 116 are in communication with the air intake chamber 1141, and the two second through holes 117 are in communication with the air outlet chamber 1142. An air adjusting ring 130 is further provided nesting the mouthpiece 110. Also referring to FIG. 3, the air adjusting ring 130 defines two gaps 131. The air adjusting ring 130 is rotatable relative to the mouthpiece 110, so that an overlapped area among the first through hole 116, the gaps 131, and the second through hole 117 can be changed, thus adjusting an air output of the air outlet 113. Air in the air passage 114 flows in a direction sequentially from the air inlet 115, the first through hole 116, the gaps 131, the second through hole 117, to the air outlet 113. The connecting end 112 includes a threaded screw structure.

Figure 3:
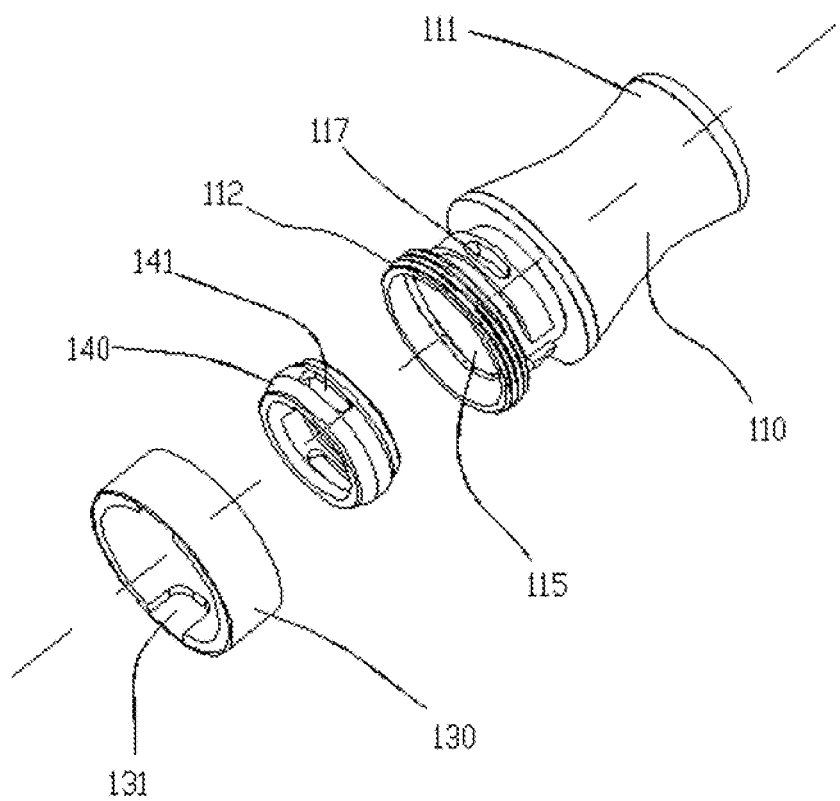
FIG. 3 is an exploded perspective view of the mouthpiece assembly of FIG. 1.

Referring to FIGS. 2-3, a sealing ring 140 is further provided between the air adjusting ring 130 and the mouthpiece 110. The sealing ring 140 defines two third through holes 141 spatially corresponding to the second through holes 117. The sealing ring 140 is configured for preventing air from leaking from a gap between the mouthpiece 110 and the air adjusting ring 130.

In the present embodiment, referring to FIG. 3, the sealing ring 140 nests a part of the mouthpiece 110 defining the second through hole 117 in such a manner, that the third through hole 141 communicates with the second through hole 117. The air adjusting ring 130 is coupled to the sealing ring 140 via interference fit, so that children are prevented from screwing the air adjusting ring 130 easily. The sealing ring 140 is made of rubber or silicone.

In the present embodiment, the air adjusting ring 130 is rotatable relative to the mouthpiece 110. In this way, an overlapped area among the first through hole 116, the gaps 131, and the second through hole 117 can be changed, thus adjusting an air output of the air outlet 113.

Figure 4:
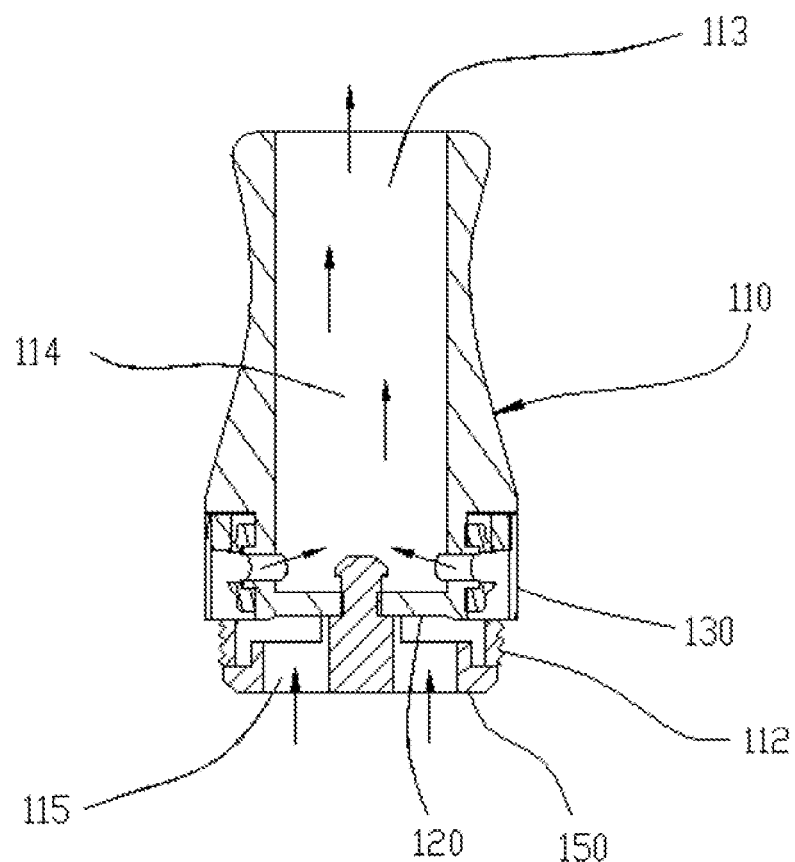
FIG. 4 is a cross-sectional view of the mouthpiece assembly with a flexible element according to a second embodiment.
Figure 5:
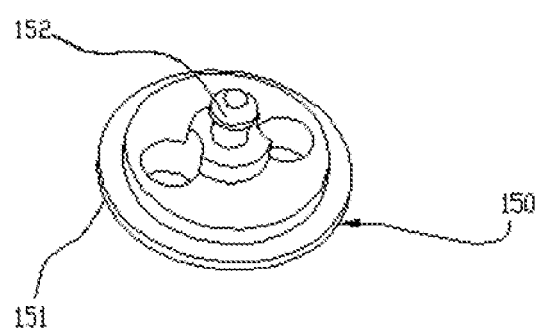
FIG. 5 is a perspective view of the flexible element of FIG. 4.
Figure 6:
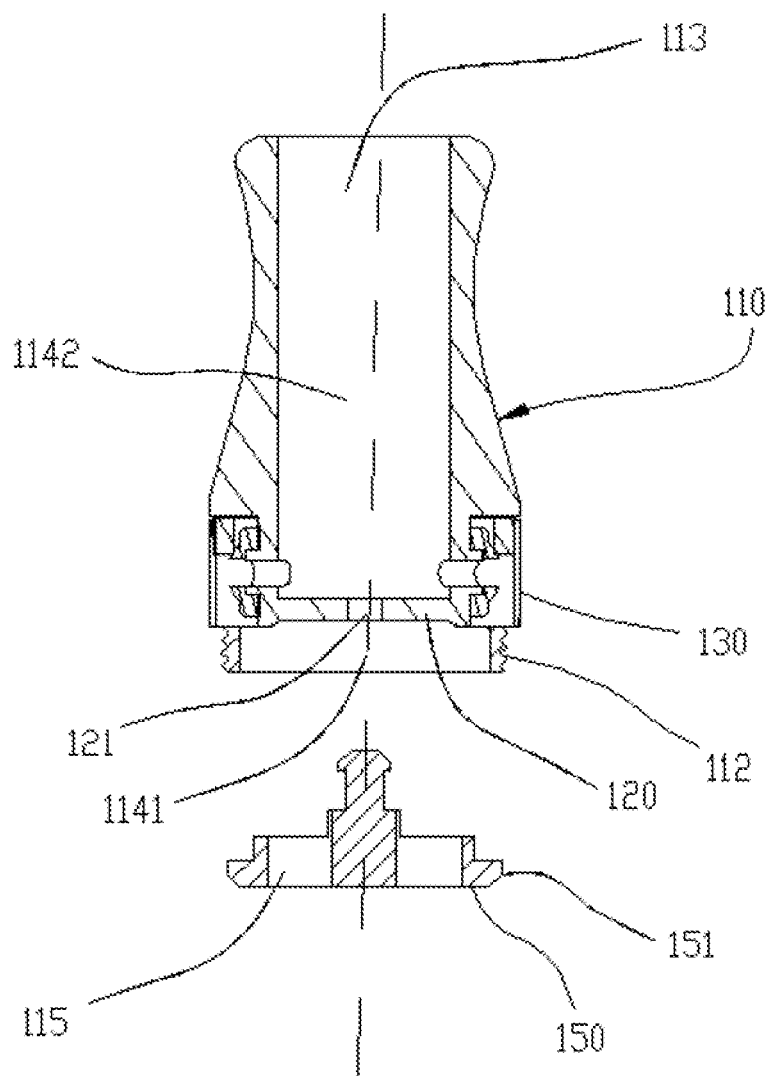
FIG. 6 is an exploded cross-sectional view of the mouthpiece assembly of FIG. 4.

In another embodiment, referring to FIGS. 4-6, a flexible element 150 is further provided at the connecting end 112, and is in the air intake chamber 1141. The air inlet 115 is defined in the flexible element 150. The flexible element 150 keeps the air inlet 115 in communication with the first through hole 116. The flexible element 150 is configured for achieving a hermetic connection between the connecting end 112 and an external component. In detail, the partition element 120 defines a connecting hole 121. The flexible element 150 includes a flange 151 and an extension end 152 matching with the connecting hole 121. The extension end 152 is engaged in the connecting hole 121, so that the flexible element 150 is fixed. The flange 151 abuts against an end surface of the connecting end 112.

Figure 7:
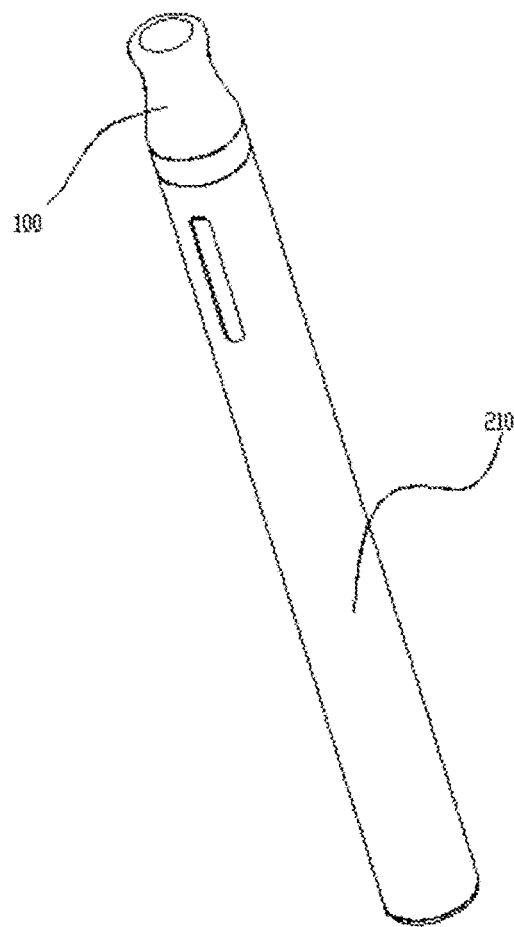
FIG. 7 is a perspective view of an electronic cigarette according to a third embodiment.
Figure 8:
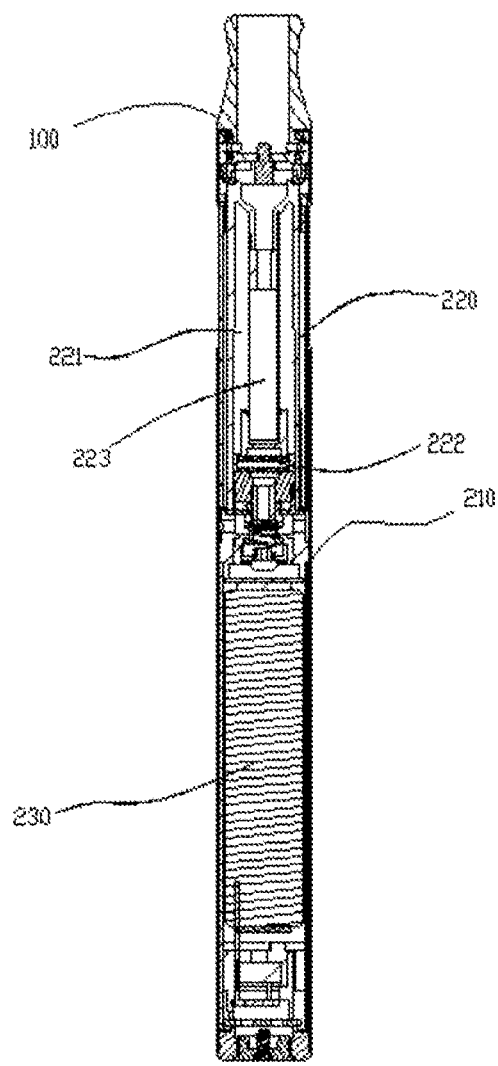
FIG. 8 is a cross-sectional view of the electronic cigarette of FIG. 7.
Figure 9:
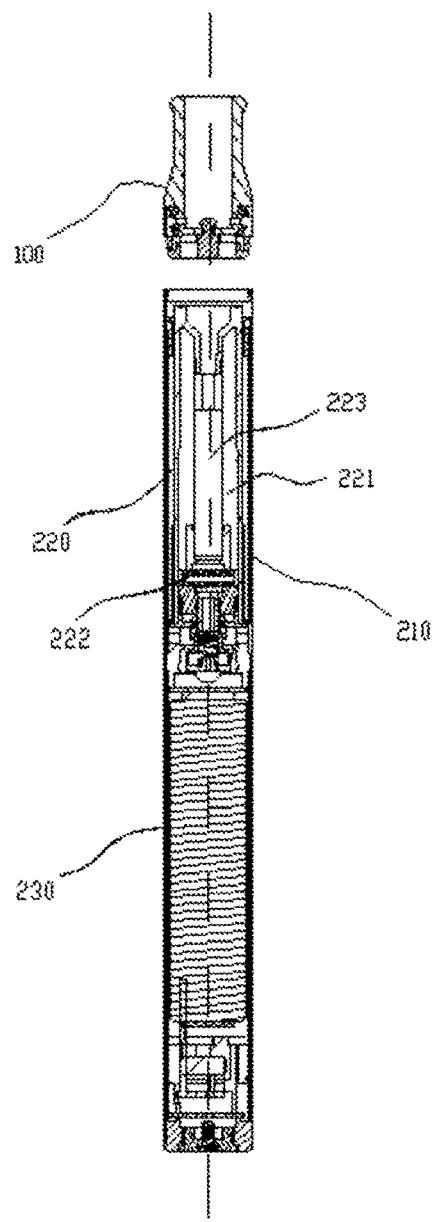
FIG. 9 is an exploded cross-sectional view of the electronic cigarette of FIG. 7.

Referring to FIGS. 7-9, an electronic cigarette is shown. The electronic cigarette includes a housing 210, the mouthpiece assembly 100 of the first embodiment, an atomizer 220 and a power supply 230. The mouthpiece assembly 100 is arranged at an end of the housing 210. The atomizer 220 and the power supply 230 are arranged in the housing 210. The power supply 230 is configured for feeding the atomizer 220 power. The atomizer 220 includes a liquid chamber 221, an atomizing element 222, and an aerosol passage 223. The liquid chamber 221 is configured for containing tobacco liquid. The atomizing element 222 is configured for atomizing the tobacco liquid to aerosol. The aerosol passage 223 allows the aerosol to pass through. The connecting end 112 is connected to an end of the housing 210, and the air passage 114 is in communication with the aerosol passage 223 (also referring to FIG. 4).

In the present embodiment, the atomizer 220 and the power supply 230 is a one-piece structure. In other embodiments, the atomizer 220 and the power supply 230 may be coupled detachably with each other.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. A mouthpiece assembly for an electronic cigarette, comprising:
   a mouthpiece, the mouthpiece comprising a sucking end, a connecting end, and an air passage, the connecting end being configured for connecting with an external component generating aerosol for user use, the sucking end defining an air outlet, the connecting end defining an air inlet for receiving the aerosol from the external component, both the air inlet and the air outlet being in communication with the air passage;
   wherein the mouthpiece assembly further comprises a partition element provided in the air passage, the partition element dividing the air passage into an air intake chamber spatially communicable with the air inlet and an air outlet chamber spatially communicable with the air outlet, the mouthpiece further comprises a sidewall defining at least one first through hole and at least one second through hole, the at least one first through hole is in communication with the air intake chamber, the at least one second through hole is in communication with the air outlet chamber, the mouthpiece assembly further comprises an air adjusting ring nesting the mouthpiece, the air adjusting ring defines at least one gap, and the air adjusting ring is rotatable relative to mouthpiece, when the air adjusting ring is rotated to a first position where an overlapped area is formed among the at least one first through hole, the at least one gap and the at least one second through hole, the aerosol from the air inlet travels in the overlapped area via passing through the at least one second through hole, the at least one gap and the at least one first through hole sequentially to reach the air outlet chamber, and when the air adjusting ring is rotated to a second position where the overlapped area does not exist, the aerosol is stopped to reach the air outlet chamber, the overlapped area among the at least one first through hole, the at least one gap and the at least one second through hole can be changed when the air adjusting ring is rotated between the first position and the second position, thus adjusting an air output of the air outlet.

2. The mouthpiece assembly according to claim 1, further comprising a sealing ring between the air adjusting ring and the mouthpiece, wherein the sealing ring is configured for preventing air from leaking from a gap between the mouthpiece and the air adjusting ring.

3. The mouthpiece assembly according to claim 2, wherein the sealing ring nests a part of the mouthpiece defining the at least one second through hole, and the air adjusting ring is coupled to the sealing ring via interference fit.

4. The mouthpiece assembly according to claim 1, wherein the connecting end comprises a threaded structure.

5. The mouthpiece assembly according to claim 1, further comprising a flexible element provided at the connecting end, wherein the flexible element is arranged in the air intake chamber, the flexible element keeps the air inlet in communication with the at least one first through hole, and the flexible element is configured for achieving a hermetic connection between the connecting end and the external component.

6. The mouthpiece assembly according to claim 5, wherein the flexible element comprises a flange, the flange abuts against an end surface of the connecting end, and the air inlet is defined in the flexible element.

7. The mouthpiece assembly according to claim 5, wherein the partition element defines a connecting hole, the flexible element further comprises an extension end matching with the connecting hole, and the extension end is engaged in the connecting hole, so that the flexible element is fixed.

8. An atomizer for an electronic cigarette, comprising:
   a housing;

a mouthpiece assembly according to claim 1, the mouthpiece assembly being arranged at an end of the housing, the connecting end being connected to an end of the housing, the air passage being in communication with the aerosol passage;

a liquid chamber defined in the housing, the liquid chamber being configured for containing tobacco liquid;

an atomizing element configured for atomizing the tobacco liquid to form aerosol; and an aerosol passage.

9. An electronic cigarette, comprising:

an atomizer according to claim 8; and a power supply configured for supplying the atomizer power.

10. A mouthpiece assembly for an electronic cigarette, comprising:

a mouthpiece, the mouthpiece comprising a sucking end, a connecting end, and an air passage, the connecting end being configured for connecting with an external component, the sucking end defining an air outlet, the connecting end defining an air inlet, both the air inlet and the air outlet being in communication with the air passage;

wherein the mouthpiece assembly further comprises a partition element provided in the air passage, the partition element dividing the air passage into an air intake chamber and an air outlet chamber, the mouthpiece further comprises a sidewall defining at least one first through hole and at least one second through hole, the at least one first through hole is in communication with the air intake chamber, the at least one second through hole is in communication with the air outlet chamber, the mouthpiece assembly further comprises an air adjusting ring nesting the mouthpiece, the air adjusting ring defines at least one gap, and the air adjusting ring is rotatable relative to mouthpiece, so that an overlapped area among the at least one first through hole, the at least one gap, and the at least one second through hole can be changed, thus adjusting an output of the air outlet;

wherein a sealing ring is between the air adjusting ring and the mouthpiece, the sealing ring is configured for preventing air from leaking from a gap between the mouthpiece and the air adjusting ring; and wherein the sealing ring nests a part of the mouthpiece defining the at least one second through hole, and the air adjusting ring is coupled to the sealing ring via interference fit.

11. A mouthpiece assembly for an electronic cigarette, comprising:

a mouthpiece, the mouthpiece comprising a sucking end, a connecting end, and an air passage, the connecting end being configured for connecting with an external component, the sucking end defining an air outlet, the connecting end defining an air inlet, both the air inlet and the air outlet being in communication with the air passage;

wherein the mouthpiece assembly further comprises a partition element provided in the air passage, the partition element dividing the air passage into an air intake chamber and an air outlet chamber, the mouthpiece further comprises a sidewall defining at least one first through hole and at least one second through hole, the at least one first through hole is in communication with the air intake chamber, the at least one second through hole is in communication with the air outlet chamber, the mouthpiece assembly further comprises an air adjusting ring nesting the mouthpiece, the air adjusting ring defines at least one gap, and the air adjusting ring is rotatable relative to mouthpiece, so that an overlapped area among the at least one first through hole, the at least one gap, and the at least one second through hole can be changed, thus adjusting an output of the air outlet;

wherein a flexible element is provided at the connecting end, the flexible element is arranged in the air intake chamber, the flexible element keeps the air inlet in communication with the at least one first through hole, and the flexible element is configured for achieving a hermetic connection between the connecting end and the external component; and wherein the partition element defines a connecting hole, the flexible element further comprises an extension end matching with the connecting hole, and the extension end is engaged in the connecting hole, so that the flexible element is fixed.

* * * * *